US009565994B2

(12) United States Patent
Kappel et al.

(10) Patent No.: US 9,565,994 B2
(45) Date of Patent: Feb. 14, 2017

(54) ELONGATE MEDICAL DEVICE WITH ARTICULATING PORTION

(71) Applicant: Boston Scientific Scimed, Inc., Maple Grove, MN (US)

(72) Inventors: Gary S. Kappel, Acton, MA (US); Francis T. MacNamara, Sunnyvale, CA (US); Federico Gutierrez, Bedford, TX (US); John Kummailil, Ashland, MA (US); Thomas M. Ragonese, Bloomington, IN (US); Robert B. DeVries, Northborough, MA (US); Paul Smith, Smithfield, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/924,999

(22) Filed: Oct. 28, 2015

(65) Prior Publication Data
US 2016/0045096 A1 Feb. 18, 2016

Related U.S. Application Data

(63) Continuation of application No. 13/945,682, filed on Jul. 18, 2013, now Pat. No. 9,204,783.
(Continued)

(51) Int. Cl.
*F16D 1/12* (2006.01)
*A61B 1/008* (2006.01)
(Continued)

(52) U.S. Cl.
CPC ........... *A61B 1/008* (2013.01); *A61B 1/00078* (2013.01); *A61B 1/00128* (2013.01);
(Continued)

(58) Field of Classification Search
CPC ... A61B 1/00128; A61B 1/0057; A61B 1/008; A61B 1/00064; A61B 1/08; A61B 1/00078; A61B 1/0011; A61M 25/0138; A61M 25/0009; G02B 23/2476; F16C 1/04; F16D 3/12; F16D 3/56; F16D 3/58
(Continued)

(56) References Cited

U.S. PATENT DOCUMENTS 1,029,355 A * 6/1912 Francke .................... F16D 3/56
464/81
1,115,299 A * 10/1914 Francke .................... F16D 3/56
464/81
(Continued)

FOREIGN PATENT DOCUMENTS

WO WO 96/38193 A1 12/1996
WO WO 2005/120326 A2 12/2005
(Continued)

OTHER PUBLICATIONS

International Search Report and Written Opinion from corresponding PCT Application No. PCT/US2013/051109, dated Jan. 20, 2014 (17 pages).

*Primary Examiner* — Josh Skroupa
(74) *Attorney, Agent, or Firm* — Bookoff McAndrews, PLLC

(57) ABSTRACT

An articulating portion for an elongate medical device is disclosed. The articulating portion may include a plurality of segments movable relative to one another, and a plurality of hinges disposed between adjacent segments. The segments can be configured to bend at the hinges upon manipulation of a control member of the device. The segments and the hinges can also be a single continuous piece of material.

20 Claims, 8 Drawing Sheets

Related U.S. Application Data

(60) Provisional application No. 61/674,008, filed on Jul. 20, 2012.

(51) Int. Cl.
| | | |
|---|---|---|
| *A61M 25/01* | (2006.01) | |
| *G02B 23/24* | (2006.01) | |
| *A61M 25/00* | (2006.01) | |
| *A61B 1/00* | (2006.01) | |

(52) U.S. Cl.
CPC .... *A61M 25/0009* (2013.01); *A61M 25/0138* (2013.01); *G02B 23/2476* (2013.01); *A61B 1/0011* (2013.01); *A61B 1/00064* (2013.01); *Y10T 403/32008* (2015.01); *Y10T 403/453* (2015.01); *Y10T 403/54* (2015.01)

(58) Field of Classification Search
USPC .............. 403/53, 119, 145, 149, 166, 220, 223,403/291; 464/51, 78–81, 86, 100, 101; 600/141, 600/142; 138/120
See application file for complete search history.

(56) References Cited

U.S. PATENT DOCUMENTS

| | | | |
|---|---|---|---|
| 1,157,148 A | 10/1915 | Bond | |
| 3,071,942 A * | 1/1963 | Alcaro | F16D 3/72 464/78 |
| 3,537,275 A * | 11/1970 | Smith | F16D 3/74 464/78 |
| 6,270,453 B1 | 8/2001 | Sakai | |
| 6,817,974 B2 * | 11/2004 | Cooper | A61B 17/00234 600/142 |
| 7,591,783 B2 * | 9/2009 | Boulais | A61B 1/008 600/141 |
| 7,678,117 B2 | 3/2010 | Hinman et al. | |
| 8,052,597 B2 | 11/2011 | Boulais | |
| 2006/0111615 A1 | 5/2006 | Danitz et al. | |
| 2008/0249364 A1 | 10/2008 | Korner | |
| 2008/0286036 A1 | 11/2008 | Macnamara | |
| 2010/0160735 A1 * | 6/2010 | Bakos | A61B 17/3417 600/141 |
| 2010/0331776 A1 | 12/2010 | Salahieh et al. | |
| 2011/0004157 A1 | 1/2011 | Dewaele et al. | |
| 2011/0070019 A1 * | 3/2011 | Song | B25J 17/0208 403/220 |

FOREIGN PATENT DOCUMENTS

| | | |
|---|---|---|
| WO | WO 2007/009093 A2 | 1/2007 |
| WO | WO 2009/098244 A2 | 8/2009 |

* cited by examiner

ELONGATE MEDICAL DEVICE WITH ARTICULATING PORTION

REFERENCE TO RELATED APPLICATIONS

The present application is a continuation of U.S. patent application Ser. No. 13/945,682, filed Jul. 18, 2013, now U.S. Pat. No. 9,204,783, which claims priority under 35 U.S.C. §119 to U.S. Provisional Application No. 61/674,008, filed Jul. 20, 2012, all of which are herein incorporated by reference in their entireties.

FIELD OF THE INVENTION

The present disclosure relates to medical devices in general, and to articulation joints for steerable medical devices in particular.

BACKGROUND OF THE INVENTION

An elongate medical device, for example, a catheter or an endoscope, is an instrument introduced into the body for examination, surgical, diagnostic, therapeutic, or other medical purposes. Such a medical device may be inserted into a patient's internal structures, such as the esophagus, stomach, lungs, colon, uterus, urethra, kidney, and other organ systems. Conventional imaging endoscopes used for such procedures can include an illuminating mechanism, such as a fiber optic light guide connected to a proximal source of light, and an imaging means such as an imaging light guide to carry an image to a remote camera, or eye piece. In some instances, a miniature video camera may be placed within the endoscope itself. Additionally, many endoscopes include one or more working channels through which medical devices, such as biopsy forceps, snares, probes, and other tools, may be passed in order to perform a procedure at a desired location in a patient's body.

Many procedures are directed to regions in the body that require an appropriately equipped medical device to be maneuverable to navigate complex and tortuous paths within a patient's body without causing trauma to the walls of the tract. To this end, such devices may include a means to deflect a distal tip, such as an articulation joint, to follow such paths. An articulation joint may be a flexible, steerable section at the tip of a medical device, such as an endoscope.

To control the deflection of the distal tip, control members, such as cables or wires, are carried within the body of the elongate medical device to connect the articulation joint adjacent the distal end to a set of control knobs at a proximal end of a handle of the device. By manipulating the control knobs or other actuator, an operator is able to control tension applied to the articulation joint to steer the device during insertion and direct it to a region of interest in the patient's body.

An articulation joint may include a series of stacked metal links held together by joints, such as pivot joints, where the links bend with respect to each other. These links may be, for example, stainless steel, and held together by a known fixation technique. For example, metal rivets or welded metal springs acting as hinge points for the links can be used. While an elongate medical device can be used in many procedures with such a design, and while metal rivets, for example, may create a robust and durable hinge point usable for numerous procedures, the number of parts and difficulties associated with automated manufacturing increase the cost of the device. Especially for disposable medical devices, it is desirable to keep costs low. Therefore, there is a need for an alternatively designed elongate medical device having an articulating portion that, among other things, can be manufactured at a lower cost. The devices described herein overcome these and/or other shortcomings in the existing technology.

SUMMARY OF THE INVENTION

In one aspect, an articulating portion for an elongate medical device is disclosed. The articulating portion may include a plurality of segments movable relative to one another, and a plurality of hinges disposed between adjacent segments. The segments can be configured to bend at the hinges upon manipulation of a control member of the device. The segments and the hinges can also be a single continuous piece of material.

In another aspect, an articulating portion for an elongate medical device is disclosed. The articulating portion may include a plurality of segments movable relative to one another, and a plurality of hinges disposed between adjacent segments. At least one of the hinges may include a flexible connecting member fixed to the adjacent segments, having at least one lumen formed therein. The segments can be configured to bend at the hinges upon manipulation of a control member of the device.

In yet another aspect, a method of manufacturing an articulating portion for an elongate medical device is disclosed. The method can include cutting a continuous shape from a sheet of material, where the continuous shape includes a plurality of strips. The method can further include rolling the shape into a tubular form, and fixing one edge of the shape to an other edge to maintain the tubular form. The plurality of strips can form hinges between adjacent segments of the articulating portion.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made to exemplary embodiment of the elongate medical device, examples of which are illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body, or closer to the user, using the medical device. In contrast, "distal" refers to a position relatively further away from the user, using the medical device, or closer to the interior of the body.

Figure 1:
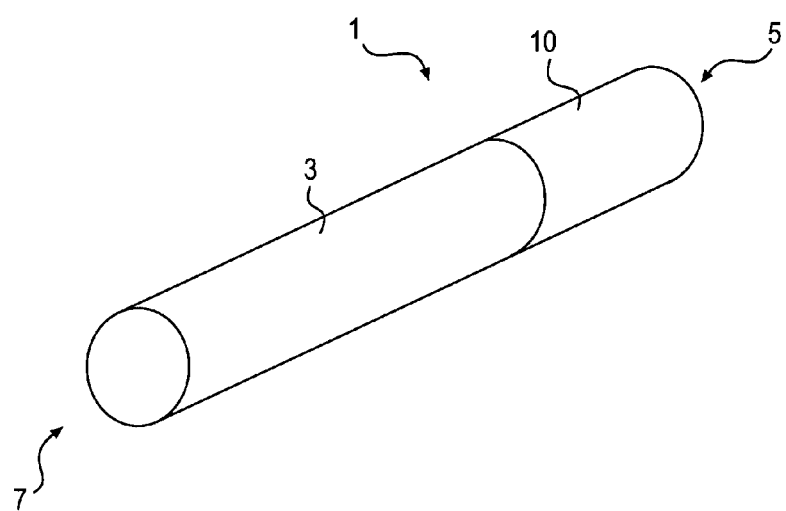
FIG. 1 is a perspective view of an elongate medical device.

FIG. 1 illustrates an elongate medical device 1, according to an exemplary embodiment. The device 1 can be an elongate medical device, such as a medical instrument or tool, guide tube, sheath, catheter, endoscope, or other like device configured to be used in any therapeutic or diagnostic procedure. The device 1 can be shaped and sized for placement into a patient via a body cavity or an incision. Furthermore, the device 1 can be configured to operate with one or more instruments (not shown) used in various medical procedures. For example, the device 1 can include one or more lumens (not shown) configured to receive a grasper, a pair of scissors, a hook, an ablation device, or another type of medical instrument. The device 1 may also be configured to operate with, or include, insufflation, irrigation, suction, imaging, or systems used in endoscopic, laparoscopic, or other medical procedures.

The device 1 may include a shaft 3 having a proximal end 7 and a distal end 5. Proximal end 7 can be manipulated by an operator to control distal end 5. For example, proximal end 7 can include one or more knobs, handles, actuators, or other devices (not shown) configured to move distal end 5 relative to the proximal end 7. The shaft 3 can also include an articulating portion 10, also referred to herein as an articulation joint. As shown in FIG. 1, the articulating portion 10 can be located at or near the distal end 5. In other embodiments, the articulating portion 10 can be located anywhere along the shaft 3, or can encompass the entire length of the shaft 3. While the device 1 can be of any shape, in some instances the shaft 3 can be cylindrical or tubular, as shown in FIG. 1, to facilitate passage into a body cavity.

Figure 2:
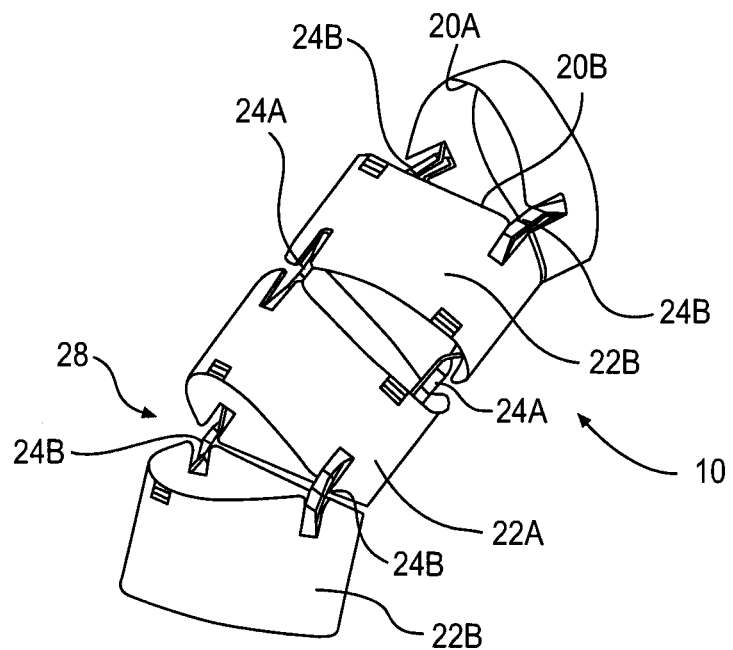
FIG. 2 is a detail of an articulating portion of the elongate medical device according to a first embodiment.
Figure 3:
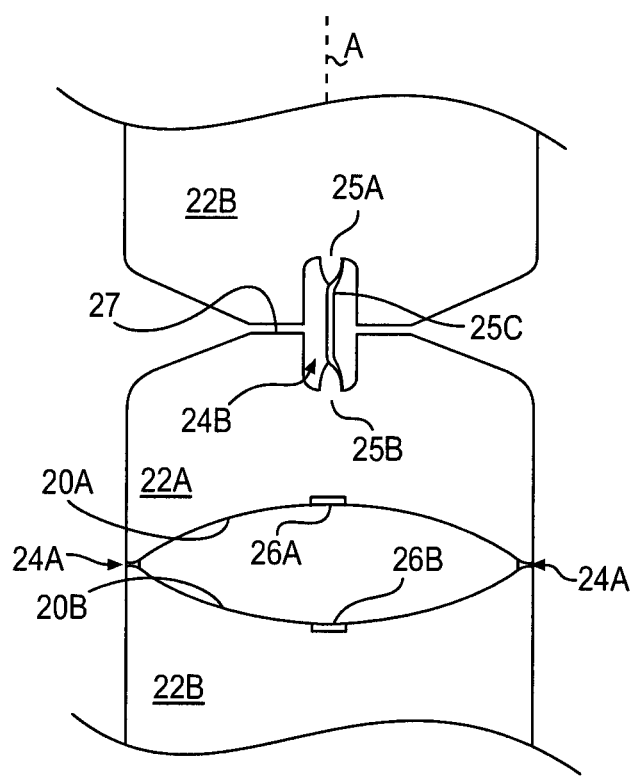
FIG. 3 is a view of a section of the articulation portion of the first embodiment.

FIGS. 2-5 depict a first embodiment of an articulating portion. The articulating portion 10 shown in this first embodiment, as well as other embodiments, is shown with a protective sheath removed to show the details of the articulating portion 10. As shown in FIGS. 2 and 3, the articulating portion 10 includes a plurality of segments, including segments 22A and 22B, positioned along a length of the body of the articulating portion 10. The articulating portion 10 can include any number of segments, depending on the particular procedure for which the medical device 1 is to be used. Additionally, the segments described with respect to additional embodiments herein can be similar to the segments 22A and 22B of the first embodiment of the articulating portion.

The articulating portion 10 also includes a plurality of hinges, including a pair of hinges 24A and 24B positioned on opposing sides of the body of the articulating portion 10 and between adjacent segments 22A and 22B. The hinges 24A, 24B are positioned within a gap defined by edges of adjacent segments 22A, 22B. Also, as shown in FIG. 3, the first end 25A of the hinge 24A, 24B, can be axially aligned with the second end 25B of hinge 24B. Although FIG. 3 shows hinge 24B, it is to be understood that hinge 24A has the same or similar structure. As described in more detail below, the hinges 24A and 24B can be integral with the segments 22A and 22B such that the entire articulating portion 10, including the segments 22A and 22B and the hinges 24A and 24B, is made of a single piece of material, such as a metal. Where the entire articulating portion 10 is made from a single piece of material, the articulating portion 10 can be referred to as "continuous" or the parts can be referred to as being "integrated" with each other. The hinges 24A and 24B, as well as the hinges described with respect to other embodiments of the device, can also be referred to herein as beams, struts, connectors, and the like.

The articulating portion 10 includes opposing rims 20A and 20B on either side of the hinges 24A and 24B. The rims 20A and 20B are contoured such that they are nearly in physical contact with each other in an area adjacent the hinges 24A and 24B, but slope away from each other to form a gaps 28, as shown in FIG. 2. The gaps 28 may be said to include the hinges 24A and 24B. The spaces between the rims 20A and 20B, that is, the size of the gaps 28, is greatest at an angle of 90 degrees with respect to the location of the hinges 24A and 24B. In some instances, the gaps 28 between the rims 20A and 20B can be, for example, V-shaped or U-shaped, such that the size of the gaps 28 is generally consistent between the adjacent rims 20A, 20B. The gaps 28 between the rims 20A, 20B allows the articulating portion 10 to bend, and the maximum width of the gaps 28 determines how much various segments of the articulating portion 10 can bend.

Figure 4:
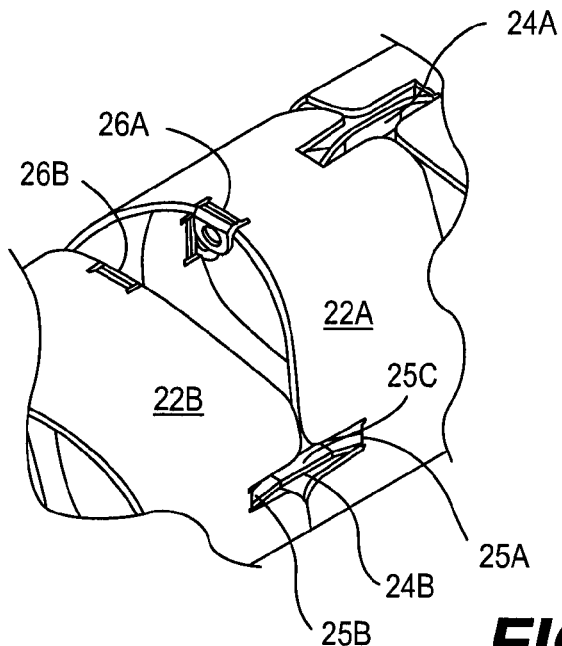
FIG. 4 shows a magnified perspective view of a section of the articulating portion of the first embodiment.
Figure 4A:
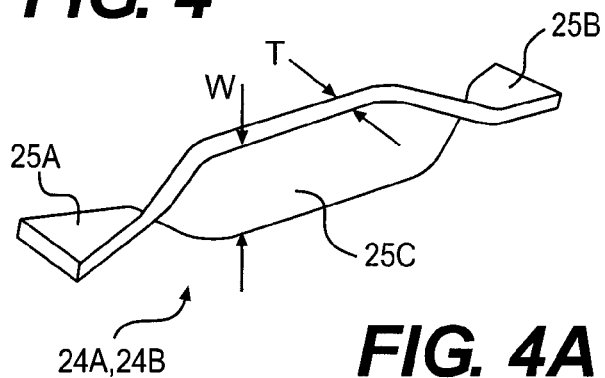
FIG. 4A shows a perspective view of a hinge according to the first embodiment.

FIG. 4 shows a magnified view of a section of the articulating portion 10 of FIG. 3, and FIG. 4A shows a perspective view of a hinge 24A, 24B. The hinge 24A, 24B of FIG. 4A is shown removed from the articulating portion 10 for clarity. As noted above, however, and as described in more detail below, the hinge 24A, 24B can be formed integrally with the entire articulating portion 10, that is, the hinge 24A, 24B can be made of the same continuous sheet of material forming the entire articulating portion 10. The hinge 24B, which can be configured similarly to hinge 24A, is formed as a strip of material, such as metal, having two ends 25A and 25B. As described in more detail below, FIGS. 4 and 4A show the strip of material of the hinge 24B having been twisted such that a central portion 25C, also referred to herein as a flat face, of the hinge 24B is oriented approximately perpendicularly to an adjacent side wall 27 of the articulating portion 10 parallel to a longitudinal axis of articulating portion 10. As shown in FIG. 4A, the hinge 24B can have two twists, each resulting in the flat strip of material to twist 90 degrees. The two ends 25A and 25B are formed integrally with the adjacent segments 22A, 22B of the articulating portion 10.

As shown in detail in FIG. 4, each segment 22A and 22B can also include one or more guide elements, or tabs, 26A and 26B. For example, segment 22A can include two tabs 26A positioned on opposite sides of the rim 20A, and two tabs 26B positioned on opposite sides of the rim 20B, thereby forming tabs along four axes of the articulating portion 10. The tabs 26A, 26B can be positioned 180 degrees apart on a side of each segment 22A or 22B. Tabs 26A on segment 22A may be positioned 90 degrees apart from tabs 26B on the same segment. The hinges 24A can also be positioned 180 degrees apart from each other, and, in a similar fashion, hinges 24B can be positioned 180 degrees apart from each other. Hinges 24A may each be positioned 90 degrees apart from hinges 24B, and, as shown in FIGS. 2 and 4, the hinges 24A, 24B can each be positioned 90 degrees from the tabs 26A, 26B.

Each tab 26A and 26B includes a hole therein configured to guide a control member (not shown) therethrough to control the deflection of the articulating portion 10, as mentioned above. The control member can be fixedly attached to typically the distalmost segment, and passes through and is moveable relative to the more proximal segments. The control member can be a cable, a wire, or other suitable elongate member.

Figure 5:
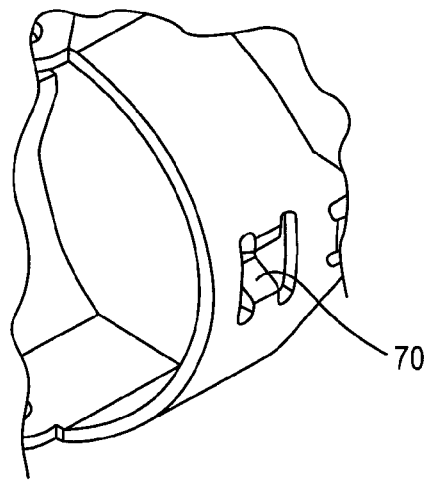
FIG. 5 shows an alternative embodiment of the guide elements according to the first embodiment of the articulating portion.

FIG. 5 shows a magnified view of a section of the articulating portion 10 employing an alternative tab embodiment. As shown in FIG. 5, at least one guide element, or tab, 70 is formed as an indented or inwardly-bent strip of the articulating portion 10 which forms a guide for the control member of the elongate medical device 1. The tab 70, which can be a plurality of tabs 70 formed along the four axes of the articulating portion 10, can act as hoops to hold and control a control member adjacent an inner circumference of the articulating portion 10. The tabs 70 can be positioned 90 degrees apart at the same axial location on a given segment 22A, 22B. Additionally, the tabs 70 can be used as anchor points to secure the distal end of a control member within the articulating portion 10. To form the tabs 70, the material forming the body of the articulating portion 10 is pushed inward, or lanced, to create guides for the control members. In other embodiments, another similar piercing operation can be used to form the tabs 70. Forming the tabs 70 as opposed to the tabs 26A and 26B can extend the life of the control member. Passing through the tab 70, the control member will be under less stress than when passing through the tabs 26A and 26B because the control member acts on a greater contact area provided by the tab 70.

Figure 6A:
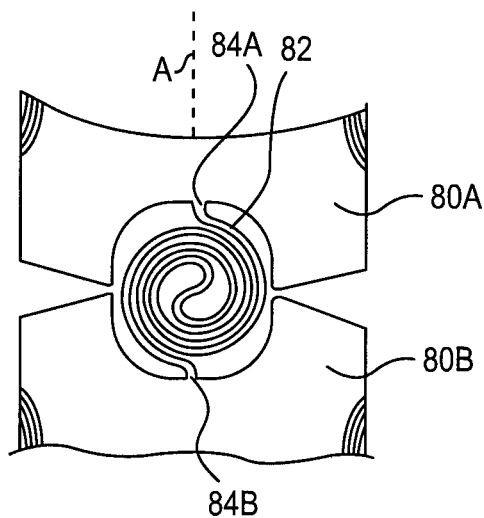
FIG. 6A is a view of a section of an articulating portion according to a second embodiment.

FIG. 6A illustrates a second embodiment of an articulating portion showing a variation on the hinge. As shown in FIG. 6A, a hinge 82 is formed between and connects two segments, 80A and 80B of the articulating portion 10. The hinge 82 is formed integrally with the segments 80A and 80B, extending from each of the segments 80A and 80B at first and second ends 84A and 84B, respectively. The hinge 82 is positioned within a gap defined by edges of the segments 80A, 80B. Also, as shown in FIG. 6A, the first end 84A of the hinge 82 can be axially aligned with the second end 84B of hinge 82.

The hinge 82 in FIG. 6A is a strip of the metal or other suitable material formed into a spiral shape of concentric loops, where the hinge 82 circles clockwise from the first end 84A to a central area between the segments 80A and 80B. This spiral shape may also be referred to as a curved or coiled shape, or the like. At the central area, the strip of metal forming the hinge 82 alters its direction, for example by 180 degrees as shown in FIG. 6A, and continues in a counterclockwise direction to the second end 84B.

Figure 6B:
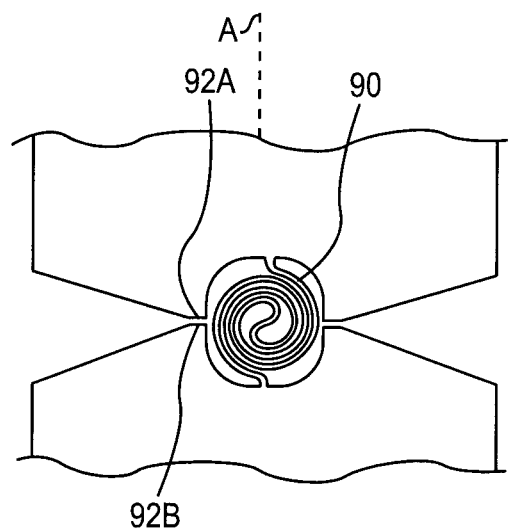
FIG. 6B is a view of a section of an articulating portion according to a modified second embodiment.

The hinge 90 in FIG. 6B is similar to the hinge 82 in FIG. 6A; however, the strip of metal (or other suitable material) forming the hinge 90 has a smaller width than that of the hinge 82. Changing the width of the strip forming the spiral hinge of the second embodiment can adjust the bending characteristics of the hinge. For instance, providing a thicker or more robust hinge, like the hinge 82, can require more force on the control members to articulate the distal end 5 of the device 1. For these reasons, the hinge of the second embodiment can be tailored to a particular medical procedure depending on a desired degree of deflection of the articulating portion by changing the width of the metal strip forming the spiral shaped hinge. The geometry of the spiral hinges 82 and 90 in FIGS. 6A and 6B can provide sufficient strength and flexibility to allow the articulating portion 10 to effectively maneuver within a body lumen.

In accordance with the second embodiment shown in FIGS. 6A and 6B, the articulating portion 10 may be susceptible to compression along its length as the control members are tensioned. Therefore, flat areas 92A and 92B are provided at a location shown in FIG. 6B. These flat areas 92A and 92B, which are edges of adjacent segments, may engage, that is, they may come into direct physical contact, when the articulating portion 10 is longitudinally compressed. Although not shown, the flat areas 92A and 92B may be included in the articulating portion shown in FIG. 6A, or in any of the embodiments of the articulating portion described herein.

Figure 7:
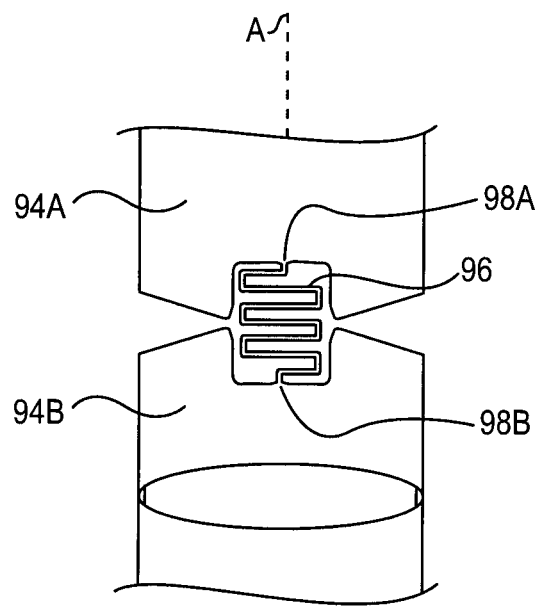
FIG. 7 is a view of a section of an articulating portion according to a third embodiment.

FIG. 7 illustrates a third embodiment of an articulating portion showing another variation on the hinge. As shown in FIG. 7, a hinge 96 is formed between and connects two segments 94A and 94B of the articulating portion 10. The hinge 96 is formed integrally with the segments 94A and 94B, extending from each of the segments 94A and 94B at first and second ends 98A and 98B, respectively. The hinge 96 in FIG. 7 is a strip of metal (or other suitable material) having a serpentine shape, which may also be referred to here as a meandering, winding, twisting, sinusoidal, or Z-shaped. As shown in FIG. 7, the hinge 96 has a series of turns, such as U-shaped turns, that alternate along the length of the hinge 96, and provide columnar strength to the articulating portion 10. The longer sides of the turns are oriented in a direction of the gap 28, that is, perpendicular to the longitudinal axis "A" of the articulating portion 10. The hinge 96 is positioned within a gap defined by edges of the segments 94A, 94B. Also, as shown in FIG. 7, the first end 98A of the hinge 96 can be axially aligned with the second end 98B of hinge 96.

Figure 8:
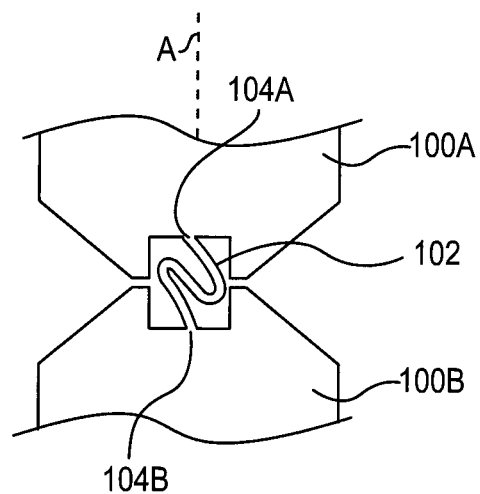
FIG. 8 is a view of a section of an articulating portion according to a fourth embodiment.

FIG. 8 shows a fourth embodiment of an articulating portion showing yet another variation on the hinge. As shown in FIG. 8, a hinge 102 is formed between and connects two segments 100A and 100B of the articulating portion 10. The hinge 102 is shown being formed integrally with the segments 100A and 100B, extending from each of the segments 100A and 100B at first and second ends 104A and 104B, respectively. The hinge 102 is a strip of metal (or other suitable material) having a serpentine shape having at least one turn, for example a U-shaped turn. As shown in FIG. 8, elongated or longer sides of the turns of the hinge 102 are oriented at an angle with respect to the longitudinal axis "A" of the articulating portion 10. For example, the longer sides of the turns of the hinge 102 can be oriented at an angle of less than 90 degrees with respect to the longitudinal axis "A" of the articulating portion 10.

The single-piece design of the articulating portion described herein optimizes flexibility and fatigue life for elongate medical devices, such as disposable endoscopes. For example, with respect to the articulating portion shown in FIGS. 2-4A, the width W and/or thickness T of the hinges 24A and 24B (FIG. 4A) can influence the flexibility and fatigue life of the articulating portion. The thickness T of the material forming the articulating portion 10 can be, for example, ½-¾ inch hard stainless steel. A desired spring beam design can be obtained using the thickness T times the width W of the articulating portion 10. Hinges that are twisted and have a greater width W, for example, can exhibit a higher fatigue life than narrower hinges. Wider hinges, however, can be less flexible, that is, they can have more bending stiffness than narrower hinges. Similarly, reducing the thickness T can enhance flexibility (i.e. the thinner the thickness T, the more flexible the hinges 24A and 24B can be), and vice versa. Additionally, where wider hinges are provided, during manufacturing the hinges may be bent inwardly to ensure that they do not exceed outer diameter requirements of the elongate medical device. Thus, the hinge width and thickness, as well as the hinge length, could be optimized to obtain a desired fatigue life and flexibility of the articulating portion. This optimization could be done at each segment of the articulating portion.

With respect to the articulating portion shown in FIGS. 6A and 6B, as noted above, the size, for example, the overall diameter, length, thickness, and width of the material of the spiral-shaped hinge, can be adjusted for optimal performance. Also, the ends of the hinges (84A and 84B) add columnar strength to the articulating portion 10, and prevent the overall length of the articulating portion 10 from shortening during bending. This ensures that the structure of the spiral-shaped hinge remains intact even when tension is applied to the steering member to compress the hinges. The spiral-shaped hinges do not generally increase bending stiffness, and the spiral design can ensure that the hinge can be designed specifically for flexibility and fatigue resistance. Specifically, the spiral geometry can minimize bending stresses, thereby promoting a longer device life and lower bending stiffness. In some instances, a braid, such as a metal braid, can be affixed to both ends of the spiral-shaped hinge to provided added torsional strength. Similar braids may be added to any of the articulating portion embodiments described herein.

With further regard to the articulating portion 10 described above, the hinges in each of these embodiments can be designed for a specific number of cycles or procedures. In some instances, the articulating portions can be designed, with an appropriate safety factor, so that they are not reusable, that is, so that each device lasts only one medical procedure. In other instances, the articulating portions can be designed so that the device can be used for a plurality of procedures.

Figure 9A:
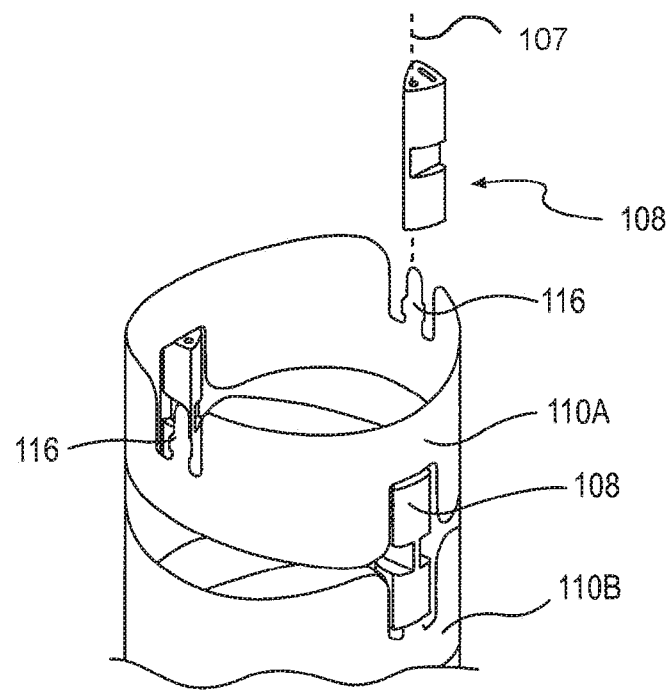
FIG. 9A is a perspective view of a section of an articulating portion according to a fifth embodiment.
Figure 9B:
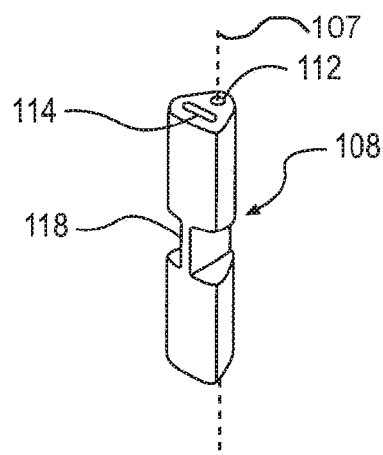
FIG. 9B is a perspective view of one of the connection members of the articulating portion according to the fifth embodiment.

FIGS. 9A and 9B depict a fifth embodiment of the articulating portion 10 of the device 1. As shown in FIG. 9A, the articulating portion 10 includes a first link 110A and a second link 110B. The links 110A and 110B can be connected together via a connection assembly, which includes a connecting member 108 and a post 116 (FIGS. 9A and 9B). The connecting member 108 and post 116 can also be referred to herein as "a hinge." The connecting member 108, which includes an opening (or slot) 114 configured to receive the post 116, can be pressed axially onto the post 116. One or both of the connecting member 108 and the post 116 can be partially or wholly made from flexible, elastomeric material, for example ultra-high-molecular-weight polyethylene ("UHMPE") or another similar material.

As shown in FIG. 9A, a plurality of connecting members 108 and posts 116 can be provided to connect adjacent segments 110A, 110B. Connecting members 108 and posts 116 connecting adjacent segments 110A, 110B can be positioned 180 degrees apart from each other and 90 degrees apart from connecting members 108 and posts 116 connecting other segments of the articulating portion 10 (FIG. 9A). Connecting members 120 and 130 and posts 122 and 132, described with respect to the sixth and seventh embodiments below, shown in FIGS. 10 and 11, respectively, can be positioned similarly.

As shown in FIG. 9A, the post 116 can be an extended portion of link 110A, 110B, and the post 116 can be barbed, that is, the post can have a barbed portion, to help secure the connecting member 108 thereto. A single connecting member 108 can receive the post 116 of the first link 110A and the post 116 of the adjacent second link 110B. As shown in FIG. 9A, the posts 116 of each link 110A and 110B can correspond to the outer diameter of the links 110A and 110B. In other instances, the posts 116 may be offset towards the middle, or interior, of the links 110A and 110B of the articulating portion. If the posts 116 are offset in this manner, when the connecting members 108 are pressed onto the posts 116 they will not increase the outer diameter of the articulating portion 10 defined by the links 110A and 110B.

In some embodiments, the opening 114 can be a through hole, extending all the way through the connecting member 108. In other embodiments, the opening 114 may be two openings 114, one on each end of the connecting member 108, where each opening 114 only extends partially through the connecting member 108. For example, the connecting member 108 may include openings 114 on both sides, each of which extends into the connecting member 108 the length of the post 116 to be disposed therein. To securely hold the connecting member 108 onto the barbed post 116, the opening 114 may also include a portion internal to the connecting member 108 to receive the barb.

As illustrated by FIGS. 9A and 9B, the connecting member 108 can have an elongated triangle-like or pyramid-like shape, or the connecting member 108 can have another suitable shape. The connecting member 108 can also include a guide hole 112 configured to receive and guide the control member, for example a control wire or cable 107, extending though an interior of the articulating portion 10. In order to guide the control member, the guide hole 112 can be a through hole, extending all the way through the connecting member 108. The guide hole 112 may be referred to herein as "a first lumen" or "one lumen," and the opening 114 may be referred to herein as "a second lumen" or "another lumen." When, as described above, the opening 114 is two openings 114, one on each side of the connecting member 108, the two openings 114 may be referred to as "a second lumen" and "a third lumen," and it may be said that the connecting member has three lumens defined therein. As shown in FIGS. 9A and 9B, the guide hole 112 may have a circular cross-sectional shape, such that the guide hole 112 has a cylindrical shape extending through the connecting member 108. The opening 114 may have a slot-like or lengthened opening extending through the connecting member 108. The guide hole 112 and the opening 114, however, are not limited to having these shapes, and in some instances the guide hole 112 and the opening 114 may have similar cross-sectional shapes.

FIG. 9B also shows the connecting member 108 including a rib 118, which can also be referred to as "a flattened portion" or "a narrowed portion." The rib 118 is an area of decreased thickness of a material centered on member 108. The rib 118 can be disposed at a center (or midpoint) of the connecting member 108 between two ends of the connecting member 108, and the rib 108 can also be disposed centrally in a width-direction of the connecting member 108. As shown in FIG. 9A, the rib 118 can be positioned in a gap defined by edges of adjacent segments 110A, 110B. The rib 118 can facilitate the flexibility of the connecting member 108, while the thicker portions of the connecting member 108 can add strength to the bending areas of the articulating portion 10. The guide hole 112 and the opening 114 may extend from each end of the connecting member 108 towards the rib 118. As noted above, the guide hole 112 may extend through the entire connecting member 108, such that the guide hole 112 extends through the rib 118. In some instances, the opening 114 may extend from each end of the connecting member 108 to a location within the connecting member 108 before reaching the rib 118. This location may correspond to the length of the post 116 so that, as described above, the opening 114 can receive the post 116.

In some instances, the connecting member 108 can include one or more metal sleeves (not shown) pressed into the guide hole 112, for example. These metal sleeves, which can have rolled edges so as not to prematurely wear the control member, can guide the control member while adding strength to the bending areas of the articulating portion 10.

The shape of the connecting member 108 and the post 116 are relatively easily cut and can be manufactured at low cost. These shapes can be formed by laser cutting in some instances, or other cutting methods in other instances. In other instances the connecting member 108 can be formed by a molding process. In yet other cases, the connecting member 108 can be extruded as a single or multi-lumen connector, thereby providing flexibility for articulation as well as a guide for the control members.

Figure 10:
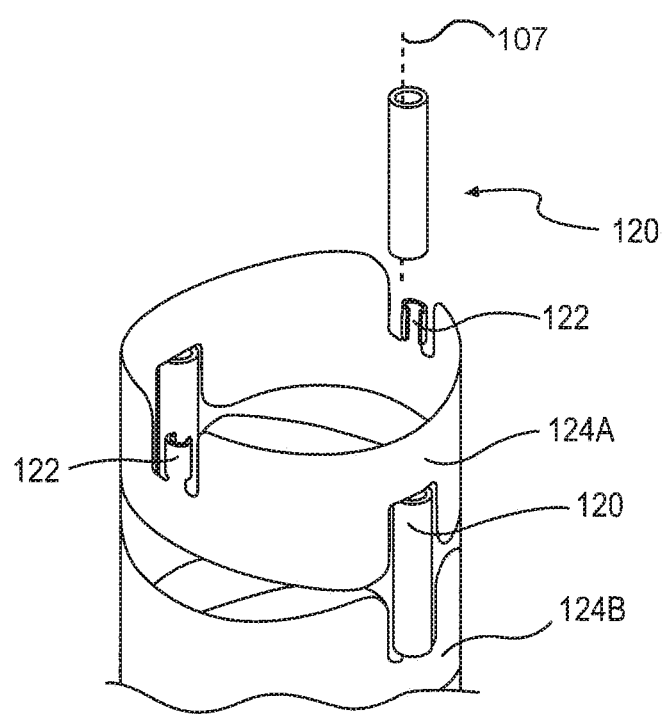
FIG. 10 is a perspective view of a section of an articulating portion according to a sixth embodiment.

FIG. 10 depicts a sixth embodiment of the articulating portion 10 of the device 1. As shown in FIG. 10, the flexible connecting member 120 is a round, single-lumen member. The connecting member 120 may be referred to herein as tubular, cylindrical, rounded, and the like. The post 122 is a rounded member extending from the link 124A or 124B and configured to receive the connecting member 120. The connecting member 120 and post 122 can also be referred to herein as "a hinge." As shown in FIG. 10, the post 122 can be a partial cylinder, that is, a cylinder having a discontinuous side wall (a side wall with a gap between edges of the side). In some instances, the post 122 may be an entire cylinder, that is, a cylinder having a continuous side wall without any gaps or breaks.

The connecting member 120 may be formed by a low-cost manufacturing method, such as extrusion, and the post 122 may be stamped then rolled into a curved shape configured to guide a control member of the device 1. In other instances the connecting member 120 could be either insert molded, snap-fit, interference fit, or friction fit, onto the posts 122. In yet other alternative, the connecting member 120 could be stamped from a flat sheet of material, then rolled and welded at a seam or an overlap to form the tubular shape shown in FIG. 10.

Figure 11:
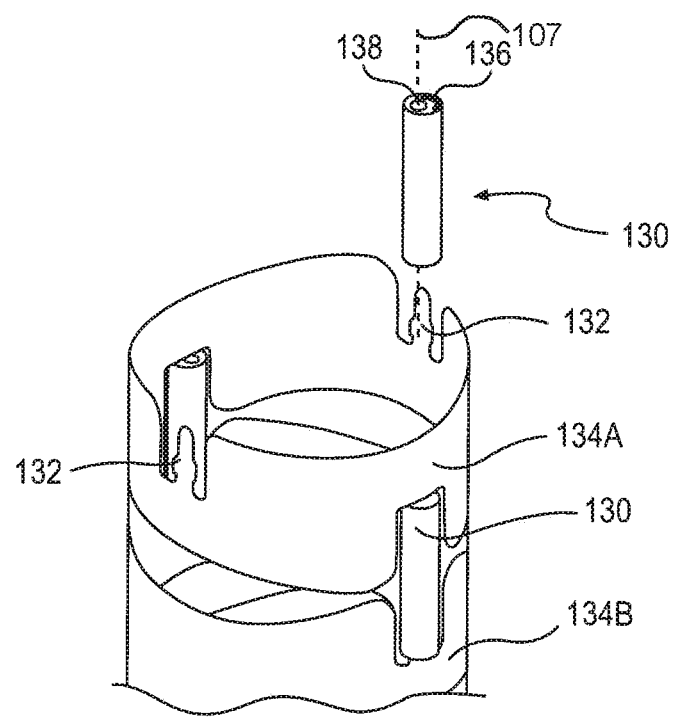
FIG. 11 is a perspective view of a section of an articulating portion according to a seventh embodiment.

FIG. 11 depicts a seventh embodiment of the articulating portion 10 of the device 1. As shown in FIG. 11, the flexible connecting member 130 is a round, multiple-lumen member. The post 132 extending from the links 134A and 134B may be a barbed post, that is, the post 132 may have a barbed portion similar to the post 116 described with respect to the fifth embodiment, shown in FIG. 9A. The connecting member 130 can include a guide hole 138 extending all the way through the connecting member 130 and configured to guide the control member, and an opening 136 configured to receive the barbed post 132. As shown in FIG. 11, the guide hole 138 may have a circular cross-sectional shape, such that the guide hole 138 has a cylindrical shape extending through the connecting member 130. The opening 136 may have a curved shape contoured to the side of the connecting member 130 and extending through the connecting member 130. The post 132 can have a corresponding curved shape, and/or be flexible to fit the curved shape of the opening 136. The guide hole 138 and the opening 136, however, are not limited to having these shapes, and in some instances the guide hole 138 and the opening 136 may have similar cross-sectional shapes. The guide hole 138 may be referred to herein as "a first lumen" or "one lumen," and the opening 136 may be referred to herein as "a second lumen" or "another lumen." The connecting member 130 and post 132 can be referred to herein as "a hinge." Similar to the connecting members 108, 120 of the fifth and sixth embodiments, respectively, the connecting member 130 can be a flexible, elastomeric component.

As shown in FIG. 11, the posts 132 of each link 134A and 134B can correspond to the outer diameter of the links 134A and 134B. In other instances, the posts 132 may be offset towards the middle, or interior, of the links 134A and 134B of the articulating portion. If the posts 132 are offset in this manner, when the connecting members 130 are pressed onto the posts 132 they will not increase the outer diameter of the articulating portion 10 defined by the links 134A and 134B.

In some embodiments, the opening 136 can be a through hole, extending all the way through the connecting member 130. In other embodiments, the opening 136 may only extend partially through the connecting member 130. For example, the connecting member 130 may include openings 136 on both sides, each of which extends into the connecting member 130 the length of the post 132 to be disposed therein. To securely hold the connecting member 130 onto the barbed post 132, the opening 136 may also include a portion internal to the connecting member 130 to receive the barb.

Like the fifth embodiment described herein, in some instances, the connecting member 130 can include one or more metal (or other suitable flexible material of sufficient strength) sleeves (not shown) pressed into the guide hole 138, for example. These metal sleeves, which can have rolled edges so as not to prematurely wear the control member, can guide the control member while adding strength to the bending areas of the articulating portion 10.

As noted above, the various embodiments of articulating portions described above, including the hinges, can be formed from a metal such as stainless steel. In some instances, the articulating portion 10 may include a braided cover made of stainless steel, Nitinol™, a plastic material such as nylon, or other biocompatible material. Where a braided cover is provided, the cover may be bonded to ends of the articulating portion, which can allow the joint to effectively transfer torque along its length. In some embodiments, for example, in the embodiments shown in FIGS. 9A-11, coils, springs, braiding, or another similar design can be provided over the articulating portion to reinforce the apparatus and to prevent cables from breaking through the material forming the articulating portion.

The articulating portions described above are broadly applicable to various medical devices and other devices requiring articulation. For example, the disclosed embodiments may be applicable to endoscopes, laparoscopes, or steerable catheters and medical tools or instruments (including endoscopic, laparoscopic, or other). Additionally, the disclosed embodiments may also be applied to devices not typically used for medical procedures, such as borescopes, which use articulation to access difficult-to-reach locations within engines or other industrial devices.

The elongate medical device 1 can be used for procedures within or adjacent to various body organs, such as an esophagus, heart, stomach, pelvic area, bladder, intestine, or gastrointestinal, urinary, or pulmonary tract. The device 1 may be configured to be inserted into a patient's body through an opening (natural opening or an incision) of a body, and the device may be pushed through the body tract.

As the device travels through the body tract, an operator can manipulate the distal end 5 of the device 1 by manipulating the articulating portion 10. Doing so moves the distal end 5 in one or more of the bending planes in three-dimensional space, that is, up, down, left, or right. Different sections of the articulating portion 10 of the device 1 may be bent in a plane to assist with the medical procedure being carried out. For instance, in some applications, the device 1 can be bent so that the curvature of the device 1 resembles the curvature of the body tract to reduce trauma to the walls of the body tract. In some instances the articulating portion 10 can be bent at its various segments in different planes to enable the device 1 to pass through an area of constriction in the body tract.

With respect to the first embodiment of the device shown in FIGS. 2-5, tensioning the control member or members (not shown) in the articulating portion can cause the flat central portion 25C of the hinges 24A and 24B to bend to maneuver the articulating portion 10. With respect to the second through fourth embodiments of the articulating portion described above, tensioning the control member or members can allow a user to maneuver the articulating portion as the segments in each embodiment move closer or further apart as the hinges bend and/or compress. With respect to the fifth through seventh embodiments of the disclosed articulating portion, tensioning the control members can cause a portion of the connection members 108, 120, and 130 to bend to maneuver the articulating portion 10.

The articulating portions of the various embodiments described above can be manufactured from a number of manufacturing methods. As one example, the hinges and the gaps between the rims, at least for the first through fourth embodiments of the articulating portion, can be cut from a single piece of metal using a laser or other suitable cutting tool. The piece of metal used to manufacture the articulating portions may be either a tube or a flat sheet of material, for example stainless steel. Where a flat sheet is used, before or after cutting, the sheet can be rolled and connected at the edges via known fixation techniques, such as welding. The tabs 26A and 26B of the first embodiment (FIG. 4) can be formed by similar methods, and may be rolled, smoothed, or polished to remove sharp edges that can cut or wear a control member passing therethrough. During cutting, the parts of material, for example metal, that form the hinges can be left in place. Doing so allows the articulating portion to be formed entirely from one piece of metal or other material. The hinges remaining after cutting can be twisted, 90 degrees for example, to allow them to flex and bend so that the articulating portion can be maneuvered. In some of the embodiments described above (FIGS. 6A, 6B, 7, and 8), the articulating portions can still be formed from a single piece of material, but the hinges can be cut into a spiral, serpentine, or other spiral-like or serpentine-like shapes, allowing them to bend and act as hinges.

As another example of a method of manufacturing an articulating portion, components of the articulating portion, for example hinges and links, can be separately formed from flat strips of metal or other material. A flat metal sheet can be cut, for example via a stamping process with a progressive die, or with a laser or other cutting tool. The cut material can then be rolled or bent and welded along a seam to form the articulating portion. Before, during, or after the material is welded, the hinges can be twisted, as described with respect to the first embodiment, to align with the direction of bending between segments of the articulating portion. If hinges are being formed in accordance with one of the second through fourth embodiments, it is not necessary (although it is an option as described below) to twist the spiral or serpentine-shaped hinges after welding the component together. As yet another example, for the articulating portions shown in FIGS. 9A, 9B, 10, and 11, the hinges may be formed as connecting members separate from individual links of the articulating portion. Where the links are separately formed, they can be produced by laser cutting a sheet or tube of stainless steel or other metal, and then joined by stacking and welding, crimping, or any other means to mechanically secure adjacent links together.

Additional alternatives to the disclosed elongate medical device with articulating portion may provide additional structural integrity. Particularly when side loads are applied to the device, the hinges may include any number of interlocking features. In certain embodiments, like those described above, where the control members may be in the same axis as the guiding elements (tabs 26A, 26B, 70), these guiding elements can be offset from the control member to reduce or eliminate the drag of the control member on the hinges.

Another alternative includes a combination of the first disclosed embodiment with one or more of the other embodiments. For example, during manufacturing, a spiral or serpentine shape or pattern may be cut into the metal, and this shape can thereafter be twisted or bent 90 degrees to form the hinges. Forming the hinges of the articulating portion in this manner can provide added flexibility as well as additional control as to the location of the pivot, or bending, point of the hinges. Furthermore, varying the geometry of the hinges in this or a similar manner can enable independent control of the bending stiffness, or flexibility, of each segment of the articulating portion. In some embodiments, controlling the bending stiffness can be used to reduce the flexibility of the distal end 5, which can in turn cause the distal end 5 to follow a tighter bending radius during articulation. This may be especially desirable in certain medical procedures where the device 1 must navigate through a constricted section of a body tract.

Conventional elongate medical devices such as catheters and endoscopes are complex instruments that are costly to manufacture and that can frequently require expensive repair as a result of damage during use or from repeated use. The various articulating portions described above enable navigation of the medical device through complex and tortuous paths, which is critical to the success of the examination, with minimum pain, side effects, risk, or sedation to the patient. Additionally, at least some embodiments of the disclosed articulating portion are manufactured entirely from one piece of material, for example a single metal tube or sheet, which reduces the number of parts, and therefore reduces the complexity of the device, which also reduces the likelihood of the device failing or needing to be repaired.

It will be apparent to those skilled in the art that various modifications and variations can be made to the disclosed elongate medical device and method. Other embodiments will be apparent to those skilled in the art from consideration of the specification and practice of the disclosed system and method. It is intended that the specification and examples be considered as exemplary only, with a true scope being indicated by the following claims and their equivalents.

What is claimed is:

1. An articulating portion for an elongate medical device, comprising:
a pair of hollow cylindrical segments, including:
a first hollow cylindrical segment, and
a second hollow cylindrical segment, wherein the second hollow cylindrical segment is movable relative to the first hollow cylindrical segment; and
a hinge assembly for coupling the first hollow cylindrical segment with the second hollow cylindrical segment, the hinge assembly including:
a first protrusion on the first hollow cylindrical segment,
a second protrusion on the second hollow cylindrical segment,
a connection member coupling the first protrusion to the second protrusion, wherein the connection member has a first opening and a second opening, the first opening receives the first protrusion, and the second opening receives the second protrusion, and wherein a flexibility of at least one of the first protrusion, the second protrusion, and the connection member allows the second hollow cylindrical segment to move relative to the hollow cylindrical first segment.

2. The articulating portion of claim 1, wherein the first opening is at a proximal end of the connection member, and the second opening is at a distal end of the connection member.

3. The articulating portion of claim 1, wherein the first protrusion includes a plate, and the first opening includes a slot for receiving the plate.

4. The articulating portion of claim 1, wherein the connection member includes a proximal portion and a distal portion connected by a narrowed intermediate portion, and the narrowed intermediate portion is narrower than the proximal portion and the distal portion.

5. The articulating portion of claim 4, wherein the narrowed intermediate portion is more flexible than at least one of the proximal portion and the distal portion.

6. The articulating portion of claim 1, wherein the connection member is a cylinder with a sidewall extending between the first opening and the second opening.

7. The articulating portion of claim 6, wherein the cylinder has a lumen extending therethrough, and the first opening and the second opening define ends of the lumen.

8. The articulating portion of claim 7, wherein at least one of the first protrusion and the second protrusion is a partial cylinder that extends into the lumen.

9. The articulating portion of claim 1, wherein at least one of the first opening and the second opening has a central longitudinal axis offset from a central longitudinal axis of the connection member.

10. The articulating portion of claim 1, wherein the first hollow cylindrical segment includes a recess, the first protrusion is within the recess, and the connection member extends into the recess to receive the first protrusion.

11. An articulating portion for an elongate medical device, comprising:
a pair of segments, including:
a first segment, and
a second segment, wherein the second segment is movable relative to the first segment;
a hinge assembly coupling the first segment to the second segment, the hinge assembly including:
a first protrusion on the first segment,
a second protrusion on the second segment,
a connection member coupling the first protrusion to the second protrusion, wherein the connection member receives the first protrusion and the second protrusion, includes a first lumen extending therethrough, and further includes a second lumen that receives at least one of the first protrusion and the second protrusion; and
a control member extending through the first lumen, wherein the control member is slidably received in the first lumen such that exertion of a force on the control member moves the second segment relative to the first segment via bending of at least one of the first protrusion, the second protrusion, and the connection member.

12. The articulating portion of claim 11, wherein the control member includes a steering wire or cable.

13. The articulating portion of claim 11, wherein the first protrusion projects distally from a surface of a first recess formed in the first segment, and the second protrusion projects proximally from a surface of a second recess formed in the second segment.

14. The articulating portion of claim 11, wherein the connection member surrounds at least one of the first protrusion and the second protrusion.

15. The articulating portion of claim 11, wherein at least one of the first protrusion and the second protrusion includes a partial cylinder.

16. An articulating portion for an elongate medical device, comprising:
a pair of segments, including:
a first segment, and
a second segment, wherein the second segment is movable relative to the first segment;
a hinge assembly coupling the first segment to the second segment, the hinge assembly including:
a first protrusion on the first segment,
a second protrusion on the second segment,
a connection member coupling the first protrusion to the second protrusion, wherein the connection member receives the first protrusion and the second protrusion, includes a lumen extending therethrough, and the first protrusion extends into the lumen; and
a control member extending through the lumen, wherein the control member is slidably received in the lumen such that exertion of a force on the control member moves the second segment relative to the first segment via bending of at least one of the first protrusion, the second protrusion, and the connection member.

17. The articulating portion of claim 16, wherein the control member includes a steering wire or cable.

18. The articulating portion of claim 16, wherein the lumen has a central longitudinal axis coaxial with a central longitudinal axis of the connection member.

19. The articulating portion of claim 16, wherein the first protrusion is in a recess of the first segment, and the connection member extends into the recess to receive the first protrusion.

20. The articulating portion of claim 16, wherein the first protrusion includes a partial cylinder that extends into the lumen.

* * * * *